(12) United States Patent
Klötzli et al.

(10) Patent No.: US 12,233,249 B2
(45) Date of Patent: Feb. 25, 2025

(54) INJECTION DEVICE WITH A CAP FOR REMOVING A NEEDLE SHIELD CAP FROM A PRODUCT CONTAINER, AND METHOD FOR ASSEMBLING SUCH AN INJECTION DEVICE

(71) Applicant: Ypsomed AG, Burgdorf (CH)

(72) Inventors: Urs Klötzli, Burgdorf (CH); Benjamin Loretz, Riedholz (CH); Thomas Fontanellaz, Zuzwil (CH); Lukas Heiniger, Lotzwil (CH); Stefan Geissbuehler, Sumiswald (CH)

(73) Assignee: Ypsomed AG, Burgdorf (CH)

( * ) Notice: Subject to any disclaimer, the term of this patent is extended or adjusted under 35 U.S.C. 154(b) by 754 days.

(21) Appl. No.: 17/477,821

(22) Filed: Sep. 17, 2021

(65) Prior Publication Data
US 2022/0001113 A1    Jan. 6, 2022

Related U.S. Application Data

(63) Continuation of application No. PCT/IB2020/051818, filed on Mar. 4, 2020.

(30) Foreign Application Priority Data

Mar. 28, 2019    (CH) .................................. 00403/19

(51) Int. Cl.
*A61M 5/32*    (2006.01)
(52) U.S. Cl.
CPC ....... *A61M 5/3204* (2013.01); *A61M 2207/00* (2013.01)

(58) Field of Classification Search
CPC .............. A61M 5/3204; A61M 5/3245; A61M 2005/3247; A61M 5/3202; A61M 5/3243; A61M 5/28
See application file for complete search history.

(56) References Cited

U.S. PATENT DOCUMENTS

| 2016/0144132 | A1 | 5/2016 | Scanlon |
| 2016/0243315 | A1 | 8/2016 | Perche et al. |
| 2017/0354789 | A1* | 12/2017 | Bendek ............. A61M 15/0001 |

(Continued)

FOREIGN PATENT DOCUMENTS

| CH | 714525 A2 | 6/2019 |
| EP | 3257540 A1 | 12/2017 |
| WO | 2017089261 A1 | 6/2017 |

(Continued)

OTHER PUBLICATIONS

English translation of International Search Report issued in International Application No. PCT/IB2020/051818, issued on May 11, 2020, 2 pages.

(Continued)

*Primary Examiner* — Nathan R Price
*Assistant Examiner* — Kayla M. Turkowski
(74) *Attorney, Agent, or Firm* — Dorsey & Whitney LLP

(57) ABSTRACT

Injection devices include a cap for removing a needle shield cap from a product container, and methods for assembling such injection devices, involve providing a cap that includes an engagement element for use in removing the needle shield cap from the product container when the cap is removed from the injection device.

20 Claims, 4 Drawing Sheets

(56) References Cited

U.S. PATENT DOCUMENTS

2019/0374727 A1* 12/2019 Dugand .............. A61M 5/3204
2021/0386938 A1* 12/2021 Mills ................... A61M 5/3204

FOREIGN PATENT DOCUMENTS

| WO | 2018053657 A1 | 9/2017 |
| WO | 2018018167 A1 | 2/2018 |
| WO | 2020194080 A1 | 10/2020 |

OTHER PUBLICATIONS

International Preliminary Report on Patentability received for International Application No. PCT/IB2020/051818, issued on Sep. 28, 2021, 9 pages.

* cited by examiner

INJECTION DEVICE WITH A CAP FOR REMOVING A NEEDLE SHIELD CAP FROM A PRODUCT CONTAINER, AND METHOD FOR ASSEMBLING SUCH AN INJECTION DEVICE

CROSS REFERENCE TO RELATED APPLICATIONS

This application claims priority to International Application No. PCT/IB2020/051818, filed Mar. 4, 2020, entitled "INJECTION DEVICE WITH A CAP FOR REMOVING A NEEDLE SHIELD CAP FROM A PRODUCT CONTAINER, AND METHOD FOR ASSEMBLING SUCH AN INJECTION DEVICE," which in turn claims priority to Swiss Patent Application No. 00403/19, filed Mar. 28, 2019, entitled "INJECTION DEVICE WITH A CAP FOR REMOVING A NEEDLE SHIELD CAP FROM A PRODUCT CONTAINER, AND METHOD FOR ASSEMBLING SUCH AN INJECTION DEVICE", each of which is incorporated by reference herein, in the entirety and for all purposes.

FIELD OF TECHNOLOGY

Implementations relate to injection devices for administering a liquid product, such as a medicament. Implementations also relate to a method for assembling and/or preparing injection devices for administering a product.

BACKGROUND

The term "medicament" includes any flowable medical formulation which is suitable for a controlled administration through a means such as a cannula or hollow needle, for example comprising a liquid, a solution, a gel or a fine suspension containing one or more medicinal active ingredients. A medicament can be a single agent composition or a premixed or co-formulated multiple agent composition from a single container. The term medicament includes drugs such as peptides (e.g., insulins, medicaments containing insulin, preparations containing GLP-1 as well as derived or analogous preparations), proteins and hormones, biologically obtained or active substances, substances based on hormones or genes, nutritional formulations, enzymes and other substances both in solid (suspended) or liquid form as well as polysaccharides, vaccines, DNA or RNA or oligonucleotides, antibodies or parts of antibodies as well as suitable basic, auxiliary and carrier substances.

Injection devices in which a pre-filled syringe is arranged are known from the prior art. The pre-filled syringe has an injection needle which is connected to the pre-filled syringe in a non-detachable manner, and via which a medicament contained in the pre-filled syringe can be dispensed. To maintain the sterility of the injection needle and the medicament of the pre-filled syringe, the injection needle is enclosed by a needle shield cap attached to the pre-filled syringe and sealed from the environment in a sterile manner. Such needle shield caps can be designed, for example, as a so-called soft needle shield (SNS) or as a rigid needle shield (RNS). A soft needle shield (SNS) consists of an elastomeric part that surrounds the injection needle. A rigid needle shield (RNS) has several parts, in particular an elastomeric cap-shaped part and a sleeve-shaped part made from a solid, i.e., non-elastomeric plastic, which accommodates the elastomeric part and is substantially inseparably connected to it.

When handling the pre-filled syringe, there is a concern that the sterility of the injection needle and the medicament is put at risk when force is exerted on the needle shield cap. This can occur, in particular, during the assembly of the injection device, in particular when the pre-filled syringe is inserted into the syringe holder of the injection device provided for this purpose, or when the injection device is transported, in particular in the event of vibrations during the transport. The insertion of the pre-filled syringe into the injection device is therefore a step that deserves special attention with regard to the sterility of the injection needle and the medicament. It is known from WO 2018/018167 A1 and US2016/0243315 A1 that when a cap-shaped pull-off element, which is also referred to as a cap and which is attached to the distal end of the injection device and closes the distal end of the injection device, is pulled off, the needle shield cap attached to the pre-filled syringe is pulled off as well, i.e., it is removed from the pre-filled syringe when the cap is removed. The needle shield cap remains in the cap. For this purpose, the cap has engagement elements which are deformed when the cap is pulled off and are brought into engagement with the needle shield cap. When the pull-off movement of the pull-off element continues, the engagement elements take the needle shield cap with them as a result of which the needle shield cap is pulled off the pre-filled syringe. To ensure that the needle shield cap can be safely pulled off by removing the cap, it is known from the prior art that the engagement elements connected to the cap come into engagement with the needle shield cap.

SUMMARY

It is an object of the present disclosure to provide an alternative injection device and an alternative method for assembling and/or preparing an injection device for administering a product, which may enable the product container to be inserted into the injection device and/or the needle shield cap to be removed from the product container without inadvertently endangering the sterility of the injection needle and the medicament.

The object is achieved with the injection device according to the present disclosure including the claims, the description and the figures.

Implementations provide a device for administering a product, namely on an injection device with a longitudinal axis (L). The injection device may be configured as a so-called autoinjector, which may include a mechanism that automatically dispenses the product, for example using an energy store, such as a spring and may cause an automatic penetration and/or retraction of the injection needle. In the case of an autoinjector, the force for dispensing the product may be provided by the energy store, such as the spring. The injection device may alternatively be configured as a manual injection device, i.e., the force for dispensing the product may be provided by muscle power, for example from the user himself. The injection device—regardless of whether it is an autoinjector or a manual injection device—may have a needle protection sleeve which, after the injection has taken place, distally protrudes over the distal end of the injection needle or may be moved into this position relative to the housing to prevent accidental access to the injection needle and thereby reduce the risk of injury. In the case of an autoinjector, the needle protection sleeve may, for example, also serve as a triggering element for triggering the dispensing of the product, where the needle protection sleeve may be displaced for this purpose in the proximal direction relative to the housing. Alternatively, the autoinjector may be triggered by pressing a trigger button on the autoinjector, where the needle protection sheath may serve as a visual protection before the autoinjector is used.

The injection device may generally include a product container with an injection needle, such as, for example, a pre-filled syringe or a common syringe known from the prior art. The product container may, for example, include a hollow cylindrical product container portion which slidably accommodates a plunger. The plunger may form a sealing gap with the inner circumference of the product container portion and may thus form a sterile barrier. The plunger may, for example, be moved in the distal direction by means of a plunger rod of the injection device for dispensing product from the product container via the injection needle. The injection needle may be formed on the product container in a non-detachable manner. The product container may, for example, have a holding portion, such as a needle holding portion, which may be arranged distal to the product container portion and may be non-detachably connected to the injection needle and thus, for example, may surround a proximal part of the injection needle. The injection needle may thus protrude from the needle holding portion in the distal direction. The needle holding portion may, for example, have a smaller outer diameter than the product container portion. The product container portion may taper towards the needle holding portion at its distal end.

As used herein, the term "distal" refers to the direction in which the tip of the injection needle points. As used herein, the term "proximal" refers to the direction opposite to the distal direction.

Furthermore, the term "along the longitudinal axis (L)" used herein includes both the term "parallel to the longitudinal axis (L)" and the term "approximately parallel to the longitudinal axis (L)."

On the product container, for example on the product container portion, a needle shield cap, such as the soft needle shield (SNS) or rigid needle shield (RNS) known from the prior art, may be attached, such as in a non-detachable manner. The needle shield cap may, for example, be attached to the product container portion in a frictional or positive manner or in a combined frictional and positive manner. The needle shield cap may enclose the injection needle and may seal the injection needle from the environment in a sterile manner. A soft needle shield (SNS) may include or consist of an elastomer, for example a part formed on a caoutchouc or rubber base, which may surround the needle. The soft needle shield (SNS) may have, on its outer circumference, a soft surface, which may be formed from a rubber or caoutchouc-like material. A rigid needle shield (RNS) may include several parts, such as an elastomeric cap-shaped inner part and a sleeve-shaped or cap-shaped outer part made from a solid, i.e., non-elastomeric plastic, which accommodates the elastomeric part and is connected to it in a substantially non-detachable manner. The outer sleeve-shaped or cap-shaped part may surround the inner cap-shaped part and may, for example, be connected to the inner cap in a non-detachable manner such that the outer and inner cap form a unit. The inner part may be formed from a harder plastic than the inner part. The outer part may, for example, be made of polyethylene, polystyrene, polypropylene or another suitable plastic. The inner part may, for example, be formed from rubber, caoutchouc or some other suitable material.

At the distal end of the injection device or a housing, such as a receiving housing of the injection device, a cap, which may also be referred to or designed as a closure cap or pull-off cap, may be attached to close the distal end of the housing or the receiving housing. The injection device may include a housing, such as a receiving housing of the injection device, for receiving the product container, where the product container includes a firmly connected injection needle and where the needle shield cap may be detachably arranged on the product container. The needle shield cap may enclose the injection needle and may seal the injection needle from the environment in a sterile manner. The cap may, for example, be frictionally and/or positively connected to, for example snapped into, the housing or receiving housing. The cap may, for example, be removable during the removal from the injection device or the housing with an axial movement or a combined axial-rotary movement of the injection device, such as the housing or receiving housing.

The injection device may further include a product container holder, which may be fixedly, such as axially and rotationally fixedly, connected to the housing of the injection device. The product container holder may be sleeve-shaped, such as cylindrically shaped. The product container holder may serve to hold the product container, where the product container may be held in the product container holder in a fixed manner, such as in an axially and a rotationally fixed manner. Alternatively, the housing and the product container holder may be configured in one piece. Alternatively, the product container holder may be arranged so as to be axially movable and/or rotatable relative to the housing.

The cap, which may be detachably provided at the distal end of the housing of the injection device, may include one or more engagement elements for removing the needle shield cap from the product container when the cap is removed from the injection device. The cap, which may be coupled to the engagement element, may be connected to the needle shield cap via the engagement element in such a way that the removal of the cap from the injection device causes the needle shield cap to be removed from the product container. For instance, at least part of the movement or the entire movement of the cap in the distal direction may be transmitted to the engagement element, which means that the engagement element is carried along by the cap so that the engagement element pulls the needle shield cap off the product container, e.g., off of the product container portion.

The engagement element may be deformable in such a way that the engagement element is movable from a spaced-apart position in which the engagement element is radially spaced from the needle shield cap into an engagement position in which the engagement element is in engagement with the needle shield cap, where the engagement element is deformed when the cap is removed. Furthermore, the engagement element may be designed in such a way that during assembly of the injection device, for instance when inserting the product container into the housing or into the product container holder, no or very few forces may act on the needle shield cap, for instance by the engagement element. This may prevent the needle shield cap from being moved relative to the product container while the product container is being inserted. This may reduce the risk of compromising the sterility of the injection needle and the medicament. This arrangement may also ensure that no or very few forces exerted by the engagement element act on the needle shield cap during the storage of the injection device.

The engagement element may be, with respect to the needle shield cap, in the spaced position, in the delivery state of the injection device. In the engagement position, the engagement element may be arranged in relation to the needle shield cap in such a way that a movement of the cap in the distal direction causes the needle shield cap to be carried along, thereby removing the needle shield cap from the product container. In the engagement position of the engagement element, the engagement element may engage or bite on or into the needle shield cap. The engagement element may engage or bite on or into a lateral surface, or on or in an edge or on or in a distal end surface or on or in a proximal end surface of the needle shield cap.

The cap may also include a sleeve element. The sleeve element and the engagement element may be arranged relative to one another in a non-rotatable manner. The sleeve element may be cylindrical and may receive the needle shield cap. The sleeve element may include a recess with a distal and a proximal edge. In the spaced-apart position, the engagement element may at least be partially undeformed, deformed or radially outwardly deformed by the distal edge of the recess of the sleeve element. The engagement element may rest in the spaced-apart position on the distal edge of the recess of the sleeve element. In the engagement position, the engagement element may at least be partially undeformed, deformed or radially inwardly deformed by the proximal edge of the recess of the sleeve element. In the engagement position, the engagement element may be at least partially pressed or pretensioned or deformed by the proximal edge of the recess of the sleeve element against the needle shield cap, for instance, radially inward against the needle shield cap.

The sleeve element may include a grip element for gripping by a user. The grip element may include one or more knobs or grooves so that the user may better grip the grip element. The grip element may be non-rotatably connected to the housing and/or the needle protection sleeve.

The sleeve element may be received by the grip element. The grip element may at least be partially or completely surround the sleeve element. The sleeve element and the grip element may be formed in one piece. The sleeve element and/or the handle element may be formed from plastic. Alternatively, the sleeve element and/or the handle element may be formed from metal.

The sleeve element and the engagement element of the cap may be formed in two pieces. In addition, the sleeve element and the engagement element may be axially movable relative to one another when the engagement element is in the spaced-apart position or, alternatively, when the engagement element is undeformed, deformed or radially outwardly deformed. The sleeve element and the engagement element may be connected to one another so as to be axially movable in the proximal direction. In addition, the sleeve element and the engagement element may be arranged in an axially fixed manner, at least in the distal direction, when the engagement element is in the engagement position. Furthermore, the sleeve element and the engagement element may be axially movable relative to one another when the engagement element moves from the spaced-apart position into the engagement position.

In some implementations, the engagement element may be hook-shaped. Alternatively, the engagement element may have a different configuration, where, in the spaced-apart position of the engagement element, the engagement element may be radially spaced from the needle shield cap, and, in the engagement position of the engagement element, the engagement element may be in an engagement with the needle shield cap. Furthermore, the engagement element may be configured such that the engagement element is deformed when the cap is removed.

The hook-shaped engagement element may have a long and a short leg. The engagement element may have one long and two short legs. The short leg may be tooth-shaped, triangular or acute-angled. The short leg may be configured in such a way that the short leg is engageable with the needle shield cap.

The engagement element may be plastically and/or elastically deformable.

An irreversible deformation is referred to herein as a plastic deformation. The deformation of a material is plastic when the material does not return to its original shape by itself. After a force or load is applied to the material, the material retains its shape. A reversible deformation is referred to as elastic deformation. A material can revert to its original state after a force or load has been applied to the material.

The engagement element may be formed from metal, such as from steel, including stainless steel or spring steel. The engagement element may be formed from a material that has a flexural strength that allows for a plastic and/or elastic deformation. For instance, the engagement element may be configured such that the engagement element is plastically and/or elastically undeformed, deformed or radially outwardly deformed in the spaced-apart position of the engagement element and plastically and/or elastically undeformed, deformed or radially inwardly deformed in the engagement position.

The long leg of the hook-shaped engagement element may be undeformed, deformed or radially outwardly deformed in the spaced-apart position of the engagement element. In addition, the long leg of the hook-shaped engagement element may be undeformed, deformed or deformed radially inward in the engagement position of the engagement element.

The short leg of the engagement element may be in an engagement with the jacket surface of the needle shield cap, such as in a permanent engagement in the engagement position of the engagement element. The surface of the needle shield cap may include one or more openings or one or more fastening means into which the engagement element can engage or bite into the engagement position of the engagement element. Alternatively, the needle shield cap may not include opening or fastening means, for instance where the engagement element is engageable or may bite into the lateral surface of the needle shield cap in the engagement position of the engagement element.

The hook-shaped engagement element may include a long and a short leg, with the long and the short leg being connected to one another. The engagement element may be formed from a stamped and bent part. The stamped and bent part may be plastically and/or elastically deformable. The stamped and bent part may be formed from metal, such as from steel, stainless steel or spring steel. The stamped and bent part may be formed from a material with a flexural strength which may allow for a plastic and/or elastic deformation.

The long leg of the engagement element may be deformable at an angle that is transverse to the longitudinal axis (L). The long leg of the engagement element may be radially inwardly or radially outwardly deformable at an angle that is transverse to the longitudinal axis (L), such as at an angle of less than 90° transverse to the longitudinal axis (L). The long leg may extend along the longitudinal axis (L), where the long leg may be deformed radially inward or radially outward, e.g., plastically and/or elastically deformed.

The short leg of the engagement element may protrude radially inward. The short leg of the engagement element may be tooth-shaped, triangular or acute-angled. The sides of the tooth-shaped, triangular or acute-angled short leg may be straight and/or curved. A tip of the tooth-shaped or triangular or acute-angled short leg of the engagement element may protrude radially inward. The tip of the short leg of the engagement element may be in an engagement with the needle shield cap in the engagement position in which the engagement element is in engagement with the needle shield cap, or at least the tip of the short leg may be in an engagement with the needle shield cap, such as a constant or permanent engagement. The short leg of the engagement element may be configured such that the short leg is engageable with the needle shield cap or may be in an engagement with the needle shield cap.

In implementations, the long leg may extend along the longitudinal axis (L), and the long and short legs of the engagement element may be connected to one another, such as plastically and/or elastically deformed so that the short leg extends radially inward from the long leg at an angle, such as at an angle relative to the longitudinal axis (L) along the longitudinal axis (L).

In some implementations, the long and short legs of the engagement element may be connected to one another in such a way that a straight side of the tooth-shaped, triangular or acute-angled short leg is connected to the long leg along the longitudinal axis (L), and the tip of the short leg of the engagement element protrudes radially inward. When removing the cap, with the engagement element in the engagement position, the tensile force may act along the straight side of the tooth-shaped, triangular or acute-angled short leg of the engagement element, with the straight side of the tooth-shaped, triangular or acute-angled short leg being connected to the long leg along the longitudinal axis (L). The length of the straight side of the tooth-shaped or triangular or acute-angled short leg, e.g., the length of the straight side of the tooth-shaped or triangular or acute-angled short leg that is connected to the long leg, may be adapted in such a way that the cap can be securely withdrawn from the injection device.

Furthermore, a plurality of short legs may be provided on the long leg. The plurality of short legs may be arranged around the longitudinal axis (L) in the circumferential direction, transversely to the longitudinal axis (L) and/or along the longitudinal axis (L). The plurality of short legs may be designed differently. For instance, the short legs may be tooth-shaped, triangular or acute-angled. The distance between the straight side and the tip of the tooth-shaped, triangular or acute-angled short leg may vary. The plurality of short legs may establish a secure engagement with or be engageable in the needle shield cap, where the needle shield cap may then be removed from the injection device. Due to the different distances between the straight side and the tip of the tooth-shaped, triangular or acute-angled short leg, the legs may engage or bite into the needle shield cap offset from the longitudinal axis (L), due to which the needle shield cap may be safely removed from the injection device. Furthermore, a symmetrical arrangement of the engagement elements or the long or the short legs may facilitate providing stability of the engagement element or the engagement elements.

The long leg of the engagement element may be deformable, for instance plastically and/or elastically, and may be at an angle of less than 90° transverse to the longitudinal axis (L), in such a way that the short leg of the engagement element is deformed from a spaced-apart position, in which the short leg of the engagement element is radially spaced from the needle shield cap to an engagement position, in which the short leg of the engagement element is in an engagement with the needle shield cap, and where the long leg of the engagement element is deformed, e.g., plastically and or elastically, when the cap is removed. The long leg of the engagement element may be plastically and/or elastically deformed in the radially inward or radially outward direction.

Alternatively or additionally, the engagement element, or at least the short leg of the engagement element, may include a fastening means which, in the engagement position of the engagement element, may establish a fixed, e.g., an axially and radially fixed, connection with the needle shield cap. The fastening means of the engagement element may form a fixed connection with the surface or with an edge of the needle shield cap. One or more openings or one or more counter-fastening means may be provided on the surface or on the edge of the needle shield cap, where the fastening means of the engagement element may establish a fixed connection with the opening or the counter-fastening means of the needle shield cap. Alternatively, the needle shield cap may not include an opening or counter-fastening means, and the fastening means of the engagement element may engage or bite into the surface or into the edge of the needle shield cap.

The cap may further include a remover element, with the remover element including the engagement element. The remover element may be sleeve-shaped or cylindrical or at least partially sleeve-shaped or cylindrical. The long leg of the engagement element may be connected to the remover element. The engagement element, or at least the long leg of the engagement element, may be attached to a distal end of the remover element. Alternatively, the engagement element may be provided in and/or on a lateral surface of the remover element, such as, in a lateral surface of the remover element. The long leg of the engagement element may be attached in and/or on the lateral surface of the remover element. The remover element and the engagement element may be connected to one another in an axially and rotationally fixed manner. The remover element and the engagement element may be configured as one piece or as two pieces. The remover element and the engagement element may be formed from the same material. The remover element and the engagement element may be formed from a stamped and bent part. The stamped and bent part may be plastically and/or elastically deformable. The stamped and bent part may be formed from metal, such as from steel, stainless steel or spring steel. The stamped and bent part may be formed from a material that has a flexural strength may allow for a plastic and/or elastic deformation. The stamped and bent part may be bent into a sleeve shape or into a cylindrical shape or at least partially into a sleeve shape or into a cylindrical shape. Alternatively, the remover element and the engagement element may be formed from different materials.

The remover element may further include one or more holding elements. The holding element may be attached to a distal end of the remover element. Alternatively, the holding element may be provided in and/or on a lateral surface of the remover element, such as, in a lateral surface of the remover element. The remover element and the holding element may be connected to one another in an axially and rotationally fixed manner. The remover element and the holding element may be configured in one piece or in two pieces. The remover element and the holding element may be formed from the same material. The remover element and the holding element may be formed from a stamped and bent part. The stamped and bent part may be plastically and/or elastically deformable. The stamped and bent part may be formed from metal, such as from steel, stainless steel or spring steel. The stamped and bent part may be formed from a material that has a flexural strength that allows for a plastic and/or elastic deformation. The stamped and bent part may be bent into a sleeve shape or into a cylindrical shape or at least partially into a sleeve shape or into a cylindrical shape. Alternatively, the remover element and the holding element may be formed from different materials.

Alternatively, the one or more holding elements may be provided on the engagement element. The engagement element and the holding element may be arranged such that they are axially offset from one another. The engagement element may be arranged more distally from the holding element. The engagement element and the holding element may be connected to one another in an axially and rotationally fixed manner. The engagement element and the holding element may be configured in one or two pieces. The engagement element and the holding element may be formed from the same material. The engagement element and the holding element may be formed from a stamped and bent part. The stamped and bent part may be plastically and/or elastically deformable. The stamped and bent part may be formed from metal, such as from steel, stainless steel or spring steel. The stamped and bent part may be formed from a material that has a flexural strength that allows for a plastic and/or elastic deformation. The stamped and bent part may be bent into a sleeve shape or into a cylindrical shape or at least partially into a sleeve shape or into a cylindrical shape. Alternatively, the engagement element and the holding element may be formed from different materials.

The holding element may be deformable or deformed in such a way that the holding element can establish a positive and/or a non-positive connection, such as a frictional connection, with the needle shield cap. Alternatively, the holding element may be deformable or deformed in such a way that the holding element can establish a positive and/or a non-positive connection, such as a frictional connection, with the housing, the needle protection sleeve or the product container holder. The holding element may protrude radially inward.

Alternatively, the holding element may also be configured in such a way that the holding element can establish a positive and/or a non-positive connection, such as a frictional connection, with the needle shield cap.

The holding element may be configured as a tab. Alternative configurations are also possible.

In implementations of the present disclosure, the sleeve element and the engagement element may be axially movable relative to one another, for example in the proximal direction, in the spaced-apart position of the engagement element. In another implementation, the sleeve element and the engagement element may be movable relative to one another when the cap is arranged on the injection device with no product container yet being accommodated in the injection device. A relative movement in the distal direction may be limited by a stop contact between the engagement element and the sleeve element, and a relative movement in the proximal direction may be limited by a stop contact between the engagement element and the housing or the product container holder. Alternatively or additionally, a relative movement in the distal direction may take place due to a non-positive connection between the engagement element and the sleeve element, such as between the long leg of the engagement element and the distal edge of the recess of the sleeve element.

In the engagement position of the engagement element, the sleeve element and the engagement element may be arranged relative to one another in an axially fixed manner, at least in the distal direction. The proximal edge of the recess of the sleeve element and the engagement element may establish a non-positive connection, and/or a positive connection and/or an engagement, such as a driving engagement. For instance, the engagement element may be carried along via the proximal edge of the recess of the sleeve element in the distal direction when the cap is removed.

In the engagement position of the engagement element, the engagement element may be axially fixedly connected to the needle shield cap at least in the distal direction, with the needle shield cap being carried along by the engagement element of the cap as the axial movement of the cap continues. In other words, removal of the cap from the injection device is executed in two steps as the cap moves relative to the housing along the longitudinal axis (L) in the distal direction, and includes a first step of a first partial movement, during which the cap is movable or moved relative to the needle shield cap, and a second step of a second partial movement, during which the needle shield cap follows the movement of the cap or is carried along by the cap.

Implementations also relate to a method for assembling injection devices and/or for preparing injection devices for the administration of a product. The injection devices may be, for example, the injection devices described herein.

In some implementations, the method involves the step of providing a housing or a receiving housing which, for example, may be part of a housing of the injection device for receiving a product container. The housing or the receiving housing may, for example, be sleeve-shaped and/or elongated.

A product container holder may be arranged in the housing. The housing and the product container holder may be connected to one another in an axially and rotationally fixed manner. Alternatively, the housing and the product container holder may be designed in one piece. The product container holder may be used to hold the product container.

The method may further include the step of providing a cap, which may be releasably attached to a distal end of the housing. The cap may include one or more engagement elements for the removal of the needle shield cap from the product container when the cap is removed from the injection device. The cap may further include a sleeve element with a recess with a distal and a proximal edge. The sleeve element and the engagement element may be arranged relative to one another in a rotationally fixed manner. The engagement element may be at least partially undeformed, deformed or radially outwardly deformed by the distal edge of the recess of the sleeve element. The engagement element may rest on the distal edge of the recess of the sleeve element. The engagement element and the sleeve element may be connected to one another via a frictional connection in an axially movable manner. The engagement element, such as the long leg of the engagement element, may, in some implementations, be inserted in a pre-deformed position and/or state in the cap or, in another embodiment of the invention, in a spaced-apart position and/or state in the cap. In the spaced-apart position, the engagement element may be radially spaced from the needle shield cap. The engagement element and the recess of the sleeve element may form the rotationally fixed connection between the engagement element and the sleeve element. For instance, the undeformed, deformed, pre-deformed or radially outwardly deformed engagement element and the recess in the sleeve element may form the non-rotatable connection between the engagement element and the sleeve element.

The sleeve element may include a grip element for gripping by the user. The sleeve element and the grip element may be connected to one another in an axially and rotationally fixed manner. Alternatively, the sleeve element and the grip element may be formed in one piece. The grip element may include one or more knobs or one or more grooves so that the user may better grip the grip element.

The cap may include one or more engagement elements for removing the needle shield cap from the product container when the cap is removed from the injection device. The engagement element(s) may be in the shape of a hook. The hook-shaped engagement element(s) may include a long and a short leg, with the long and the short leg being connected to one another. The engagement element, or at least the long leg of the engagement element, may be deformable, such as plastically and/or elastically deformable. The engagement element may be formed from a stamped and bent part. The stamped and bent part may be plastically and/or elastically deformable. The stamped and bent part may be formed from metal, such as from steel, stainless steel or spring steel. The stamped and bent part may be formed from a material with a flexural strength which may permit a plastic and/or elastic deformation.

The long leg of the engagement element may be deformable at an angle that is transverse to the longitudinal axis (L). The long leg of the engagement element can be radially inwardly or radially outwardly deformable at an angle transverse to the longitudinal axis (L), such as at an angle of less than 90° transverse to the longitudinal axis (L). The long leg may extend along the longitudinal axis (L), where the long leg may be deformed radially inward or radially outward, such as plastically and/or elastically deformed.

In some implementations, the long leg may extend along the longitudinal axis (L), and the long and short legs of the engagement element may be connected to one another, such as plastically and/or elastically deformed, so that the short leg extends radially inward from the long leg at an angle, such as at an angle to the longitudinal axis (L) along the longitudinal axis (L). Further, the long and short legs of the engagement element may be connected to one another in such a way that a straight side of the tooth-shaped, triangular or acute-angled short leg is connected to the long leg along the longitudinal axis (L), and the tip of the short leg of the engagement element protrudes radially inward. When removing the cap, with the engagement element in the engagement position, the tensile force may act along the straight side of the tooth-shaped, triangular or acute-angled short leg of the engagement element, with the straight side of the tooth-shaped, triangular or acute-angled short leg being connected to the long leg along the longitudinal axis (L). The length of the straight side of the tooth-shaped or triangular or acute-angled short leg, such as the length of the straight side of the tooth-shaped or triangular or acute-angled short leg that is connected to the long leg, may be adapted in such a way that the cap may be securely withdrawn from the injection device.

The engagement element, or at least the short leg of the engagement element, may also be configured in such a way that the engagement element, or at least the short leg of the engagement element, may grip or bite into the needle shield cap. For instance, the engagement element, or at least the short leg of the engagement element, may grip or bite on or into a lateral surface, or on or in an edge or on or in a distal end face or on or in a proximal end face of the needle shield cap.

The cap may further include a remover element, with the engagement element arranged on the remover element. The long leg of the engagement element may be connected to the remover element. The remover element and the engagement element may be provided as one or two pieces. The engagement element and/or the remover element may be formed from a different material than the sleeve element. The sleeve element may be made of plastic. The engagement element and the remover element may be formed from the same material, such as metal.

The cap may also have one or more holding elements. The holding element(s) may be attached to the remover element or to the engagement element. The holding element may be connected to the remover element or to the engagement element in an axial and non-rotatable manner. The remover element or the engagement element and the holding element may be provided in one or two pieces. The remover element or the engagement element and the holding element may be formed from the same material. The remover element or the engagement element and the holding element may be formed from a stamped and bent part. The stamped and bent part may be plastically and/or elastically deformable. The stamped and bent part may be formed from metal, such as from steel, including stainless steel or spring steel. The stamped and bent part may be formed from a material that has a flexural strength that allows for a plastic and/or elastic deformation. The stamped and bent part may be bent into a sleeve shape or into a cylindrical shape or at least partially into a sleeve shape or into a cylindrical shape. Alternatively, the remover element and the engagement element and the holding element may be formed from different materials.

The holding element may be deformable or deformed in such a way that the holding element can form a positive and/or a non-positive connection, such as a frictional connection, with the needle shield cap. The holding element may protrude radially inward. The holding element may be configured as a tab.

Alternatively, the holding element may also be configured in such a way that the holding element can form a positive and/or a non-positive connection, such as a frictional connection, with the needle shield cap.

The method may further include the step of attaching the cap to the distal end of the housing. The cap may be snapped onto the housing, for example. The cap may be releasably attached to the distal end of the housing in such a way that the sleeve element and the engagement element are axially movable relative to one another. A relative movement in the distal direction may be limited by a stop contact between the engagement element and the sleeve element, and a relative movement in the proximal direction may be limited by a stop contact between the engagement element and the housing or the product container holder. Alternatively or additionally, a relative movement in the distal direction may take place due to a non-positive connection between the engagement element and the sleeve element, such as between the long leg of the engagement element and the distal edge of the recess of the sleeve element.

In another embodiment of the present disclosure, the method may include the step of providing a housing for receiving a product container. A product container holder may be arranged in the housing. The housing and the product container holder may be connected to one another in an axially and rotationally fixed manner. Alternatively, the housing and the product container holder may be configured as one piece. The product container holder may be used to hold the product container.

Alternatively, the method can include the step of providing the product container holder for receiving a product container with an injection needle.

The method may further include the step of providing an engagement element. The engagement element may be configured to be undeformed, deformed or radially outwardly deformed. The engagement element may be used to remove a needle shield cap from the product container. The engagement element may be deformable in such a way that the needle shield cap, which is detachably attached to the product container, may be removed.

In a further step, the housing and/or the product container holder may be placed on an assembly tool, such as a mandrel. In a further step, the engagement element may be placed on the housing and/or the product container holder, with the assembly tool, e.g., the mandrel, holding the housing and/or the product container holder and the engagement element.

In a further step, a sleeve element and/or a grip element, which may be gripped by a user, may be releasably connected, e.g., snapped, to a needle protection sleeve in a frictionally and/or positively locking manner. Alternatively, the sleeve element and/or the grip element may be releasably connected to, e.g., snapped onto, the housing in a frictional and/or positively locking manner. The sleeve element may include a recess with a distal edge and a proximal edge.

In a further step, the sleeve element and the engagement element may be joined together. The sleeve element and the engagement element may be joined together in such a way that the engagement element, or at least the long leg of the engagement element, comes to rest on the distal edge of the recess. Alternatively, the sleeve element and the engagement element may be joined together, where, in a further step, an assembly tool, such as a spreader tool, may deform the engagement element, or at least the long leg of the engagement element, in such a way that the engagement element, e.g., the long leg of the engagement element, can come to rest on the distal edge of the recess of the sleeve element.

The method may further include the step of providing the product container, which may include a firmly connected injection needle, where a needle shield cap may be detachably arranged on the product container, which may thus enclose the injection needle and seal the injection needle from the environment in a sterile manner. The product container may, for example, be a pre-filled syringe or a normal syringe known from the prior art. The product container may, for example, comprise a hollow cylindrical product container portion, where a plunger may be displaceably arranged in the product container. The plunger may be used, for example, to dispense, by means of a plunger rod of the injection device, the product from the product container via the injection needle. The injection needle may be formed on the product container in a non-detachable manner. Furthermore, the product container may include a holding portion, such as a needle holding portion, which may be arranged distal to the product container portion and non-detachably connected to the injection needle. The needle holding portion of the product container may surround a proximal part of the injection needle. The injection needle may thus protrude from the needle holding portion in the distal direction. The needle holding portion may have a smaller outer diameter than the product container portion. The product container portion may taper towards the needle holding portion at its distal end. On the product container, e.g., on the product container portion of the product container, the needle shield cap may be arranged, which may enclose the injection needle and seal the injection needle off from the environment, for instance in a sterile manner.

The method may further include the step of moving or inserting the product container with the releasably connected needle shield cap into the housing in a distal direction along a longitudinal axis (L), where the engagement element, or at least the long leg of the engagement element, is undeformed, deformed, pre-deformed or radially outwardly deformed in such a way that when the product container is displaced or inserted relative to the housing in the distal direction, the needle shield cap may be radially spaced apart from the engagement element or radially spaced apart even further. This may ensure that no or very few forces are exerted on the needle shield cap when the product container is inserted. This may prevent the needle shield cap from being moved relative to the product container while the product container is inserted. This may also reduce the risk of compromising the sterility of the injection needle and the medicament.

When the product container with the detachably connected needle shield cap is moved or inserted into the housing in the distal direction along the longitudinal axis (L), the holding element contact the needle shield cap. A positive and/or a non-positive connection, such as a frictional connection, may be established between the holding element and the needle shield cap. Alternatively, a positive and/or a non-positive connection, such as a frictional connection, may be established between the holding element and the housing, the needle protection sleeve or the product container holder. Because of the axially fixed connection between the holding element and the engagement element, the engagement element may be moved relative to the sleeve element in the distal direction. The engagement element, e.g., the long leg of the engagement element, may be undeformed, deformed or radially outwardly deformed in such a way that when the product container is displaced relative to the housing in the distal direction, the needle shield cap may be radially spaced from the engagement element, e.g., from the long leg of the engagement element, or may be spaced even further radially. The engagement element, e.g., the long leg of the engagement element, may be undeformed, deformed or radially outwardly deformed in such a way that the engagement element may reach at least the spaced-apart position.

The engagement element, or at least the long leg of the engagement element, may be deformed in such a way that the engagement element, or at least the short leg of the engagement element, may be brought into engagement with the needle shield cap during the removal of the cap from the injection device, where the engagement element, e.g., the long leg of the engagement element, may be least partially undeformed, deformed or radially inwardly deformed by the proximal edge of the recess of the sleeve element. The engagement element, or at least the long leg of the engagement element, may be moved, pressed or pretensioned or deformed in the engagement position at least partially by the proximal edge of the recess of the sleeve element against the needle shield cap, e.g., radially inwardly against the needle shield cap.

When removing the cap from the housing, the user may grip either the sleeve element or the handle element. The cap may be removed from the housing by means of an axial movement in the distal direction or by means of a combined axial and rotary movement in the distal direction. The sleeve element and the engagement element may be axially movable relative to one another until the engagement element, for instance, the long leg of the engagement element, establishes a non-positive and/or positive connection and/or engagement, which may be a driving engagement, with the proximal edge of the recess of the sleeve element. The proximal edge of the recess of the sleeve element and the engagement element, such as the long leg of the engagement element, may form the non-positive and/or the positive connection and/or the engagement, such as the driving engagement.

In the engagement position of the engagement element, the engagement element may be axially fixedly connected to the needle shield cap, and the needle shield cap may be carried along by the engagement element of the cap during continued the axial movement of the cap in the distal direction. The engagement element or a portion thereof, such as the short leg of the engagement element, may engage or bite on or into the needle shield cap, such as on or into a lateral surface or on or into an edge, a distal end face or a proximal end face of the needle shield cap. Furthermore, the sleeve element and the engagement element may be axially fixed, at least in the distal direction, by the non-positive and/or the positive connection and/or the engagement, for instance due to the driving engagement.

In other words, the movement that the cap executes when removed from the injection device relative to the housing along the longitudinal axis (L) in the distal direction may include a first partial movement, during which the cap is movable or moved relative to the needle shield cap, and a second partial movement, during which the needle shield cap follows the movement of the cap or is carried along by the cap.

The needle shield cap may remain in the cap due to the engagement element and/or the holding element and can be disposed of.

Furthermore, a needle protection sleeve may be provided, which may protrude distally over the distal end of the injection needle before or after the injection has taken place. The needle protection sleeve may be used to prevent accidental access to the injection needle.

The needle protection sleeve may be at least accommodated in the housing. Alternatively, the cap may, for example, be frictionally and/or positively connected to, for example snapped into, the needle protection sleeve.

Additional references are made to the features disclosed in connection with the device described herein, which also further develop the device for the method of assembling the injection devices and/or for preparing injection devices for the administration of a product.

BRIEF DESCRIPTION OF THE DRAWINGS

Implementations are described herein in connection with the attached figures, which are intended to show the basic possibilities of the disclosed implementations and are in no way intended to be interpreted as restrictive. The figures show the following.

DETAILED DESCRIPTION

Figure 1:
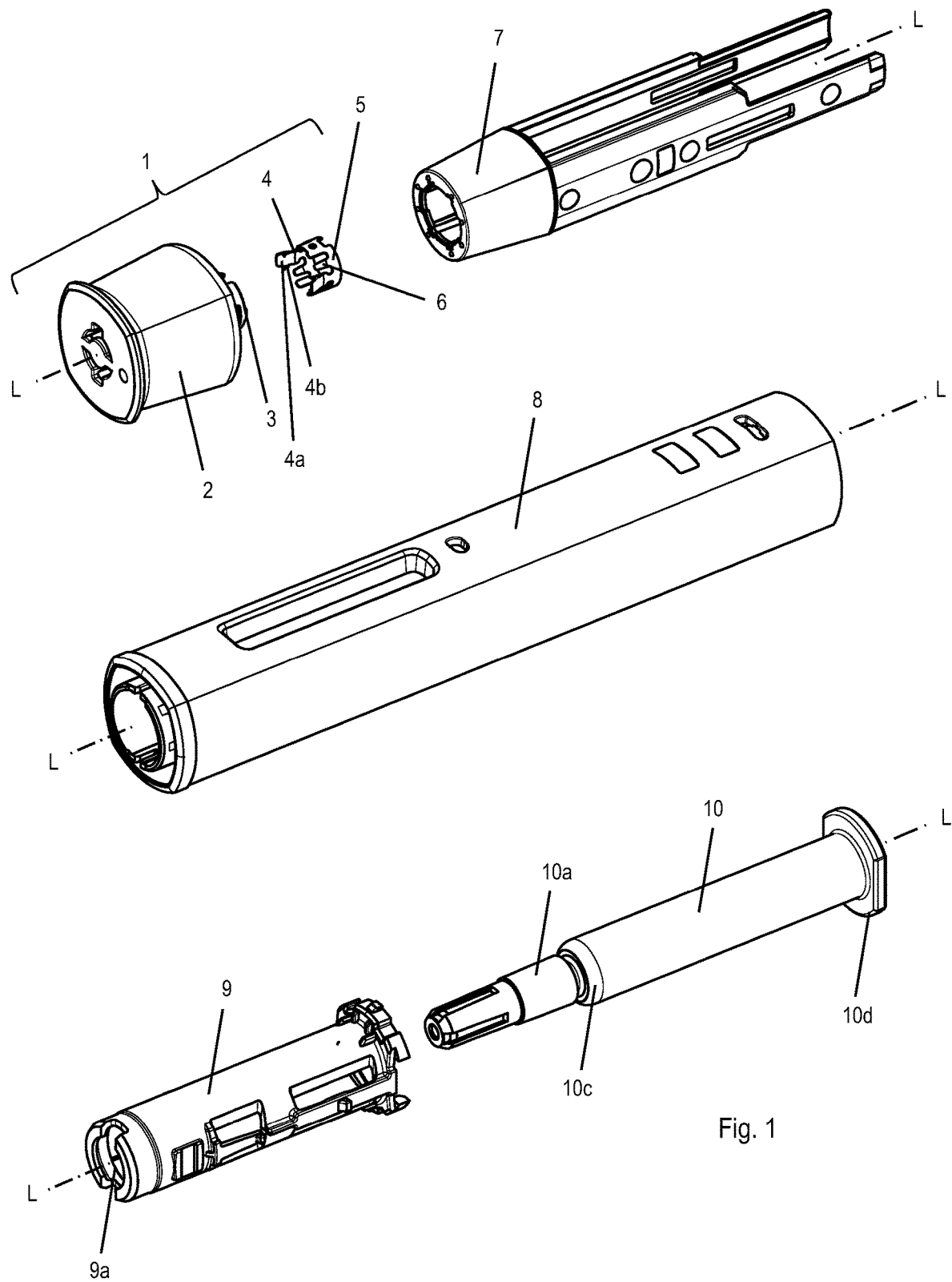
FIG. 1 is an exploded view of an injection device with a longitudinal axis (L) according to implementations of the present disclosure.
Figure 2:
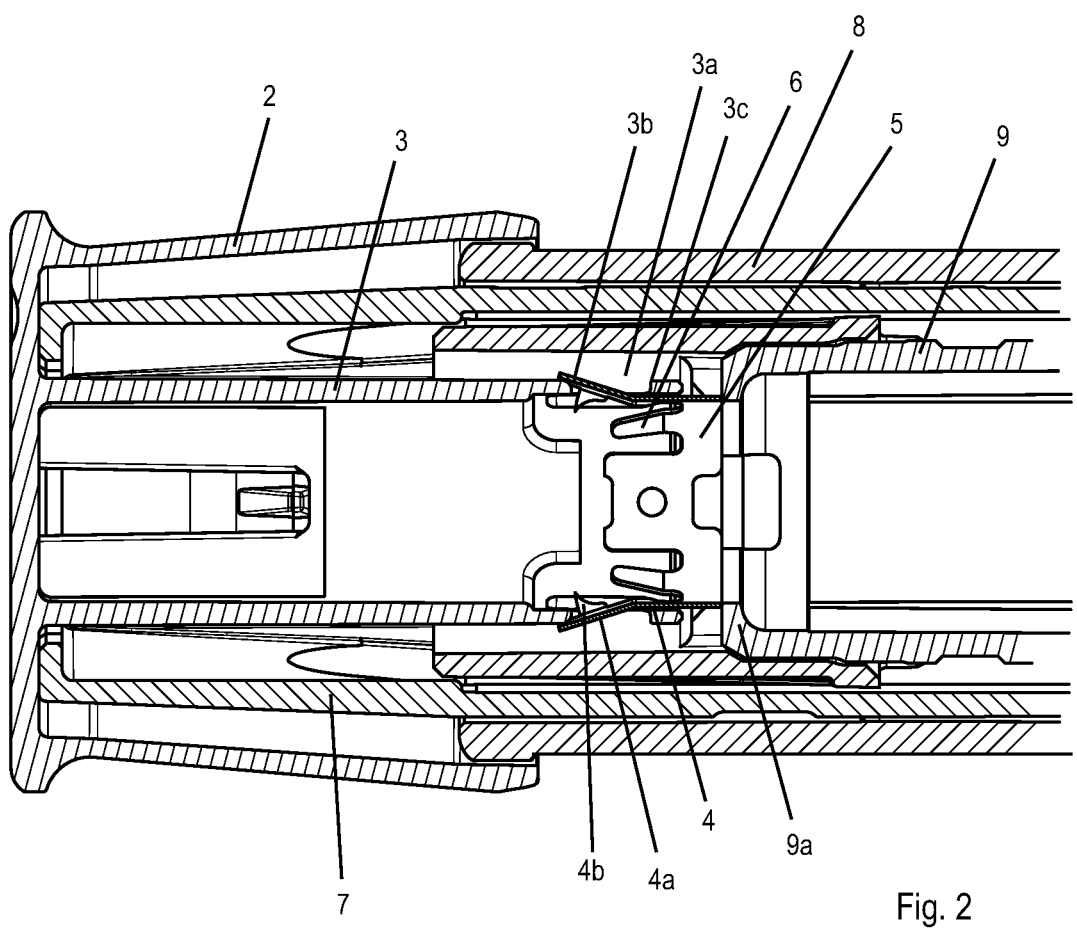
FIG. 2 is a longitudinal cross-sectional view of a distal part of the injection device of FIG. 1, with a cap being arranged on the housing of the injection device.

FIG. 1 is an exploded view of an injection device according to the present disclosure, with a cap (1) being detachably arranged on the injection device. In a delivery state, for example, the injection device may have the cap (1) placed on the distal end. The injection device may include a housing (8). The housing (8) may be configured as a sleeve-shaped housing, such as a cylindrical receiving housing with a distal and a proximal part. The injection device may further include a product container holder (9), which may be sleeve-shaped, and for instance may be a cylindrical product container holder (9). The product container holder (9) may be fixedly connected to the housing (8) of the injection device, such as axially and rotationally fixedly connected to the housing (8) of the injection device. The product container holder (9) may hold a product container (10), for instance in a fixed manner, such as in an axially and/or a rotationally fixed manner. A tapering portion of the product container portion (10c) may be supported on an inwardly protruding shoulder (9a) of the product container holder (9) in the distal direction. Alternatively, a flange (10d) of the product container (10) may be supported on the product container holder (9) in the distal direction. As an even further alternative, the product container holder (9) may hold the product container portion (10c) of the product container (10) in a frictionally engaged manner. The product container holder (9) may be arranged in the housing (8) of the injection device in an axially fixed or displaceable manner. Alternatively, the housing (8) and the product container holder (9) may be configured in one piece. Alternatively, the product container holder (9) may be arranged so as to be axially movable and/or rotatable relative to the housing (8). Furthermore, an injection needle (FIG. 3a; 10b) may arranged in the product container (10) and fixedly attached thereto (e.g., integrally constructed, non-detachable, or firmly attached), where the injection needle (10b) may be enclosed by a detachable needle shield cap (10a) for sealing the injection needle (10b) from the environment in a sterile manner. The cap (1) may be detachably provided at the distal end of the housing (8). The cap (1) may be releasably attached to the distal end of the housing (8) or, alternatively, may be releasably attached to the distal end of a needle protection sleeve (7) via a positive and/or non-positive connection, such as a snap connection. The needle protection sleeve (7) may be used to protrude distally over the distal end of the injection needle (10b) before or after the injection has taken place, or may be moved into this position relative to the housing (8) for preventing accidental access to the injection needle (10b) and may thereby reduce the risk of injury. Alternatively, the injection device may be configured without a needle protection sleeve (7). By moving the cap (1) along the longitudinal axis (L), the positive and/or non-positive connection, such as a snap connection between the cap (1) and the housing (8) or alternatively the needle protection sleeve (7) of the injection device, may be released, which causes the cap (1) to be removable from the housing (8) of the injection device in the distal direction. The distal end of the cap (1) may be closed or substantially closed so that access from the outside into the interior of the cap (1) is prevented or only possible with difficulty. The cap (1) may include a sleeve element (3). The sleeve element (3)

may include a recess (FIG. 3b; 3a), and the recess (3a) may include a distal edge (FIG. 2; 3b) and a proximal edge (FIG. 2; 3c). A grip element (2) may be provided on the sleeve element (3) in an axially and rotationally fixed manner. The sleeve element (3) and the grip element (2) may be formed in one piece. The grip element (2) may at least partially surround the sleeve element (3). The grip element (2) may be used to remove the cap (1) from the injection device, such as from the housing (8) or from the needle protection sleeve (7). Alternatively, the grip element (2) and the sleeve element (3) may be formed in two pieces. The cap (1) may further include one or more, such as two, engagement elements (4) for removing the needle shield cap (10a) from the product container (10) when the cap (1) is removed from the injection device. The distal edge (3b) and the proximal edge (3c) of the recess (3a) of the sleeve element (3) may be configured to interact with the engagement element (4) as described further herein. The engagement element (4) may be deformable such that the engagement element (4) can grip the needle shield cap (10a) and take the needle shield cap (10a) with the cap (1) when the cap (1) is removed. The engagement element (4) may be plastically and/elastically deformable. The engagement element (4) and the sleeve element (3) may be connected to one another in a rotationally fixed manner. The cap (1) may further include a remover element (5). The remover element (5) may include the engagement element (4), and the remover element (5) and the engagement element (4) may be formed in one piece. The remover element (5) and the engagement element (4) may be formed from a material which is plastically and/or elastically deformable. The remover element (5) and the engagement element (4) may be formed from a stamped and bent part, such as from a stamped and bent metal, including steel, stainless steel or spring steel. The stamped and bent part may be formed from a material with a flexural strength which may permit a plastic and/or elastic deformation thereof. Alternatively, the remover element (5) and the engagement element (4) may be formed in two pieces. The cap (1) may also include a holding element (6). The remover element (5) may include the holding element (6). The remover element (5) and the holding element (6) may be formed in one piece. The holding element (6) and the remover element (5) and/or the engagement element (4) may be made of the same material. The holding element (6) may establish a frictional and/or positive connection with the needle shield cap (10a). The holding element (6) may be configured as a tab. The engagement element (4) may be hook-shaped. The engagement element (4) may include a long leg (4a) and a short leg (4b). The short leg (4b) of the engagement element (4) may be tooth-shaped, triangular or acute-angled. The short leg (4b) of the engagement element (4) may be configured in such a way that the short leg (4b) is engageable with the needle shield cap (10a). The long leg (4a) of the engagement element (4) may be plastically and/or elastically deformed, such as plastically and/or elastically deformed in the radially inward and/or radially outward direction. The long leg (4a) of the engagement element (4) may be arranged at the distal end of the remover element (5). The long leg (4a) of the engagement element (4) may form a non-rotatable connection with the recess (3a) of the sleeve element (3).

FIG. 2 is a longitudinal cross-sectional view of the distal part of the injection device from FIG. 1, with the cap (FIG. 1; 1) being arranged on the housing (8). The representation of FIG. 2 may represent a step for assembling the injection device and/or preparing the injection device for the administration of a product.

In implementations, the housing (8) for receiving the product container (FIG. 3a; 10) may be provided in one step. A product container holder (9) may be provided in the housing (8). The cap (1) may be provided in a further step. The engagement element (4) may be inserted into the sleeve element (3) of the cap (1) such that the long leg (4a) of the engagement element (4) rests on the distal edge (3b) of the recess (3a) of the sleeve element (3). The engagement element (4), or at least the long leg (4a) of the engagement element (4), may be deformed, such as radially outwardly deformed, by the distal edge (3b) of the recess (3a) of the sleeve element (3) as illustrated in FIG. 2. The cap (1) may be releasably attached to the distal end of the housing (8). The cap (1) may be releasably connected to the housing (8) with a snap connection. Alternative connections may also be provided. The engagement element (4) may be accommodated such that the engagement element (4) is axially movable relative to the sleeve element (3). A relative movement of the engagement element (4) in the distal direction may be limited by a stop contact between the engagement element (4) and the sleeve element (3), and a relative movement of the engagement element (4) in the proximal direction may be limited by a stop contact between the engagement element (4) and the housing (8) or the product container holder (9). For instance, a relative movement of the engagement element (4) in the distal direction may be limited by a stop contact between the short leg (4b) of the engagement element (4) and the distal edge (3b) of the recess (3a) of the sleeve element (3), and a relative movement in the proximal direction may be limited by a stop contact between the remover element (5) and the housing (8) or the product container holder (9), which remover element (5) may be connected to or formed as one piece with the engagement element (4). Alternatively or additionally, a relative movement of the engagement element (4) in the distal direction may result from a non-positive connection between the engagement element (4), or at least the long leg (4a) of the engagement element (4) and the distal edge (3b) of the recess (3a) of the sleeve element (3). In implementations, the engagement element (4), or at least the long leg (4a) of the engagement element (4), may be deformed in such a way that the engagement element (4), or at least the short leg (4b) of the engagement element (4), is in the spaced-apart position and/or has moved to the spaced-apart position. In other implementations, the engagement element (4), or at least the long leg (4a) of the engagement element (4), may be pre-deformed and for instance may be in the spaced-apart position.

Figure 3A:
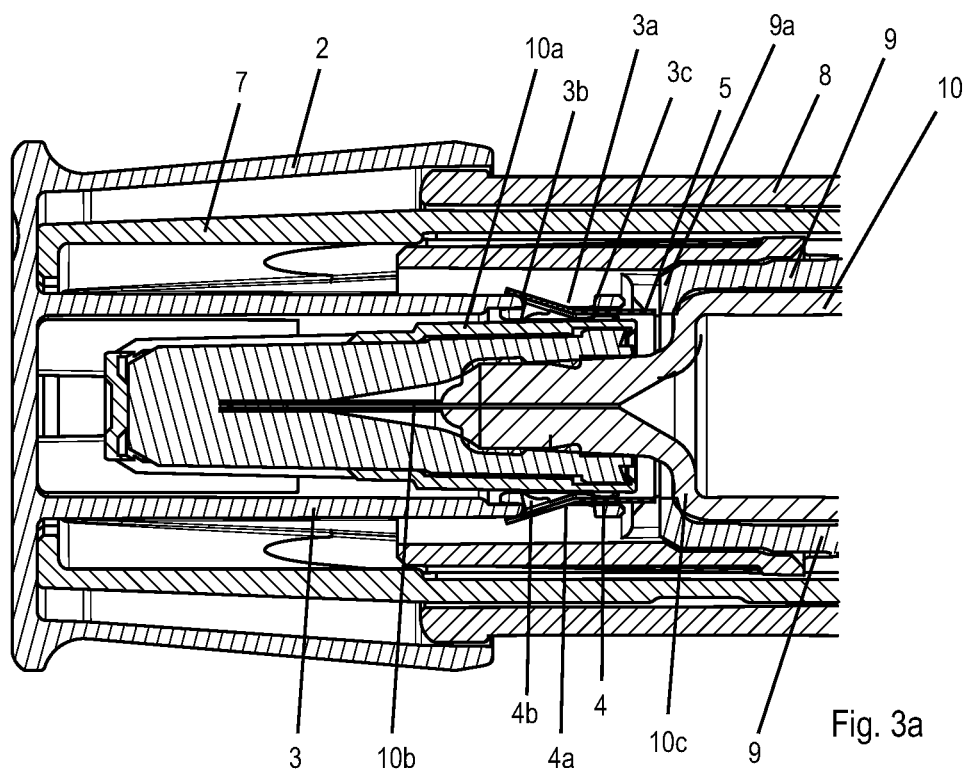
FIG. 3a is a longitudinal cross-sectional view of the distal part of the injection device of FIG. 1, with a product container having a needle shield cap enclosing an injection needle being accommodated in the cap.

In other implementations, the method may include providing a housing (8) and/or a product container holder (9) for receiving a product container (FIG. 3a; 10).

The method may further include the step of providing an engagement element (4). The engagement element (4) may be configured to be undeformed, deformed or radially outwardly deformed. The engagement element (4) may be used to remove a needle shield cap (FIG. 3a; 10a) from the product container (10).

In a further step, the housing (8) and/or the product container holder (9) may be placed on an assembly tool, such as a mandrel. In a further step, the engagement element (4) may be placed on the housing (8) and/or the product container holder (9), with the assembly tool holding the housing (8) and/or the product container holder (9) and the engagement element (4).

In a further step, a sleeve element (3), which may include a grip element (2) for gripping by a user, may be releasably connected, such as snapped, to a needle protection sleeve (7)

in a frictionally and/or positively locking manner. The sleeve element (3) may include a recess (3a) with a distal (3b) and a proximal edge (3c) as provided herein.

In a further step, the sleeve element (3) and the engagement element (4) may be joined together. The sleeve element (3) and the engagement element (4) may be joined together such that the engagement element (4), or at least the long leg (4a) of the engagement element (4), rests on the distal edge (3b) of the recess (3a) as illustrated in FIG. 2. Alternatively, the sleeve element (3) and the engagement element (4) may be joined together, where, in a further step, an assembly tool, such as a spreader tool, deforms the engagement element (4), or at least the long leg (4a) of the engagement element (4), in such a way that the engagement element (4), or at least the long leg (4a) of the engagement element (4), rests on the distal edge (3b) of the recess (3a) of the sleeve element (3).

Figure 3B:
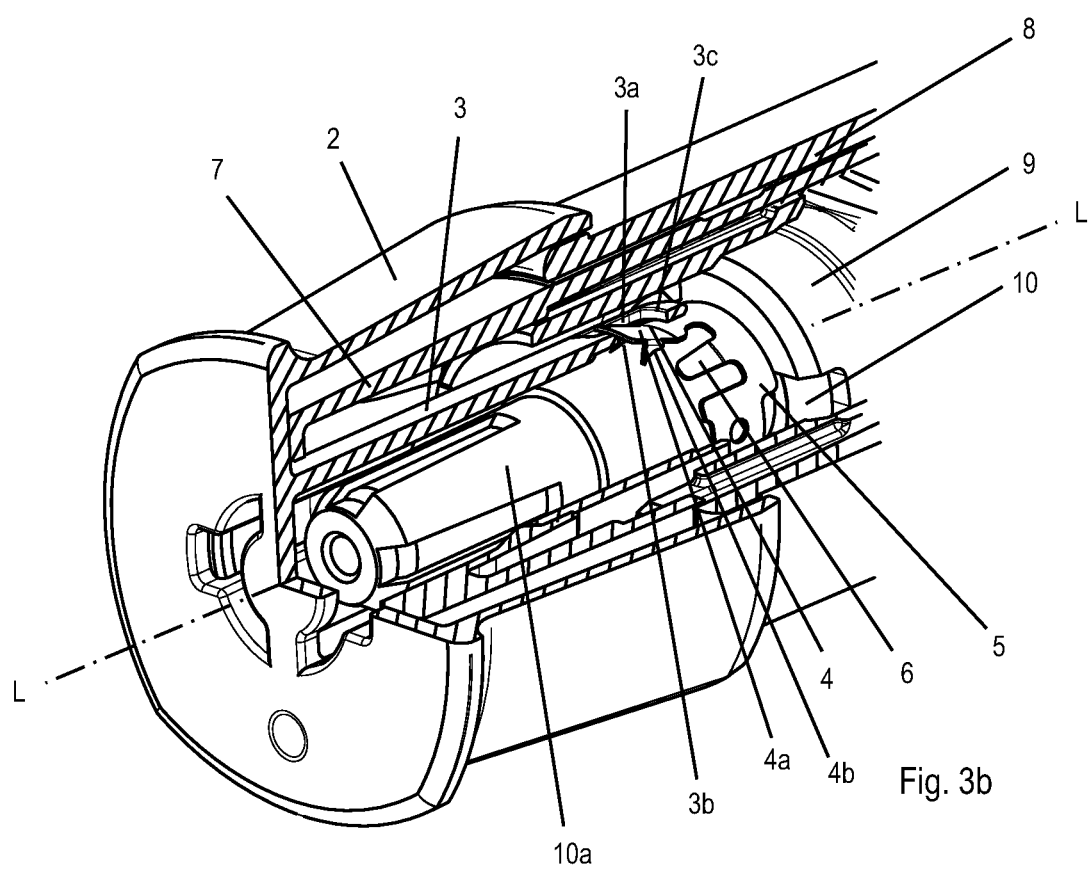
FIG. 3b is an isometric view of the distal part of the injection device of FIG. 3a, in which a part of the housing, the sleeve element, and the needle protection sleeve have been omitted.

FIG. 3a illustrates a longitudinal cross-sectional view of the distal part of the injection device of FIG. 1, with a product container (10), having a needle shield cap (10a) that encloses an injection needle (10b), being accommodated in the cap (FIG. 1; 1). FIG. 3b illustrates an isometric view of the distal part of the injection device of FIG. 3a, with a portion of the housing (8), the sleeve element (3) and the needle protection sleeve (7) being omitted. The illustrations of FIGS. 3a and 3b may represent a step for assembling the injection device and/or preparing the injection device for the administration of a product.

Accordingly, in a further step, the product container (10) may be provided with a firmly, fixedly or non-detachably connected injection needle (10b), with the needle shield cap (10a) being detachably arranged on the product container (10). On the product container (10), or at least on the product container portion (10c) of the product container (10), the needle shield cap (10a) may be detachably arranged, which may enclose the injection needle (10b) and seals the injection needle (10b) off from the environment in a sterile manner.

Furthermore, the product container (10) with the detachably connected needle shield cap (10a) may displaced in the distal direction or inserted into the housing (8) along the longitudinal axis (L). The engagement element (4), or at least the long leg (4a) of the engagement element (4), may be deformed or radially outwardly deformed in such a way that when the product container (10) is displaced or inserted relative to the housing (8) in the distal direction, the needle shield cap (10a) is radially spaced apart from the engagement element (4) or, alternatively, spaced even further apart from the engagement element (4). This may ensure that no or very few forces are exerted on the needle shield cap (10a) when the product container (10) is inserted into the housing (8). This may prevent the needle shield cap (10a) from being moved relative to the product container (10) while the product container (10) is being inserted. This may reduce the risk of compromising the sterility of the injection needle (10b) and the medicament.

When the product container (10) with the detachably connected needle shield cap (10a) is moved or inserted into the housing (8) in the distal direction along the longitudinal axis (L), the holding element (6) may contact the needle shield cap (10a). A positive and/or a non-positive connection, such as a frictional connection, may be established between the holding element (6) and the needle shield cap (10a). Because of the axially fixed connection between the holding element (6) and the engagement element (4), the engagement element (4) may be moved relative to the sleeve element (3) in the distal direction. The engagement element (4), or at least the long leg (4a) of the engagement element (4), may be deformed, for instance deformed radially outwardly, in such a way that when the product container (10) is moved relative to the housing (8) in the distal direction, the needle shield cap (10a) may be radially spaced from the engagement element (4), such as radially spaced from the long leg (4a) of the engagement element (4). The engagement element (4), or at least the long leg (4a) of the engagement element (4), may be deformed, for instance deformed radially outwardly such that the engagement element (4) moves into the spaced-apart position or, alternatively, may be further deformed radially outwardly. In this position, the injection device may be in the delivery state.

In an alternative implementations, the sleeve element (3) may, in a further step, be axially moved in the opposite direction relative to the housing (8) or the product container holder (9) so that the engagement element (4), or at least the short leg (4b) of the engagement element (4), slides from or partially from the distal edge (3b) of the recess (3a) of the sleeve element (3) and engages with the needle shield cap (10a). In this position, the injection device may be in the delivery state.

Figure 4A:
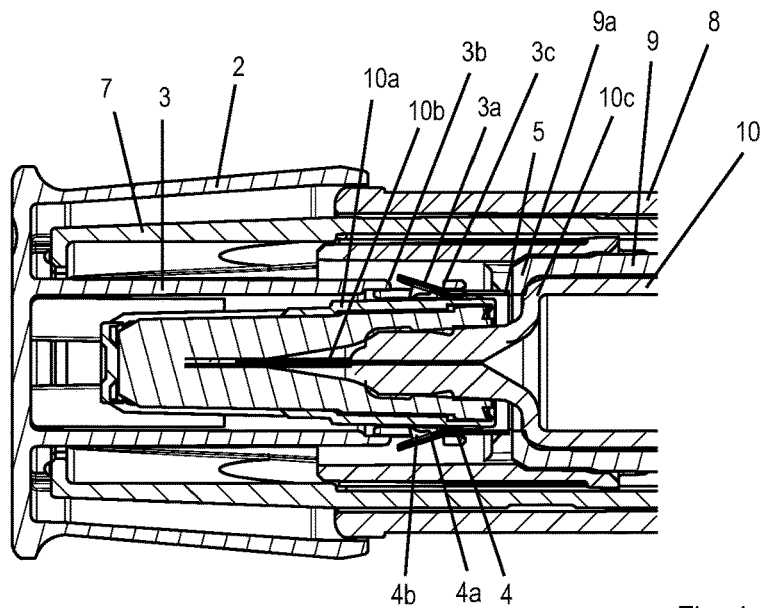
FIGS. 4a, 4b and 4c are longitudinal cross-sectional views of the distal part of the injection device from FIG. 1, showing the process of removing the cap from the injection device.
Figure 4B:
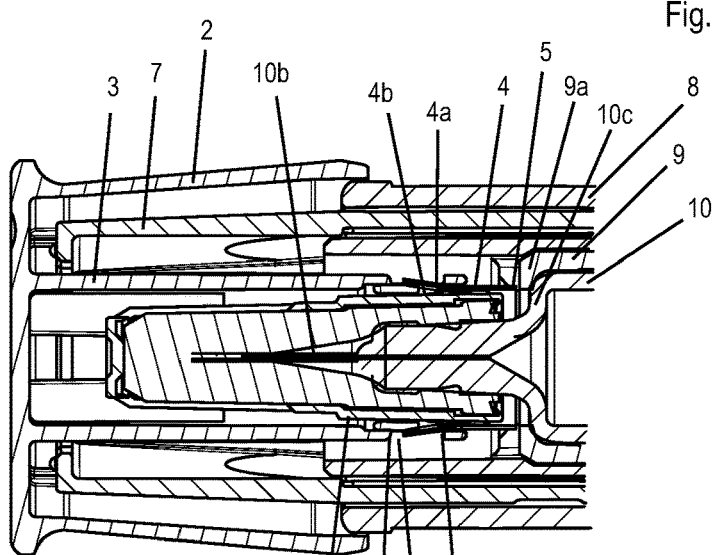
Figure 4C:
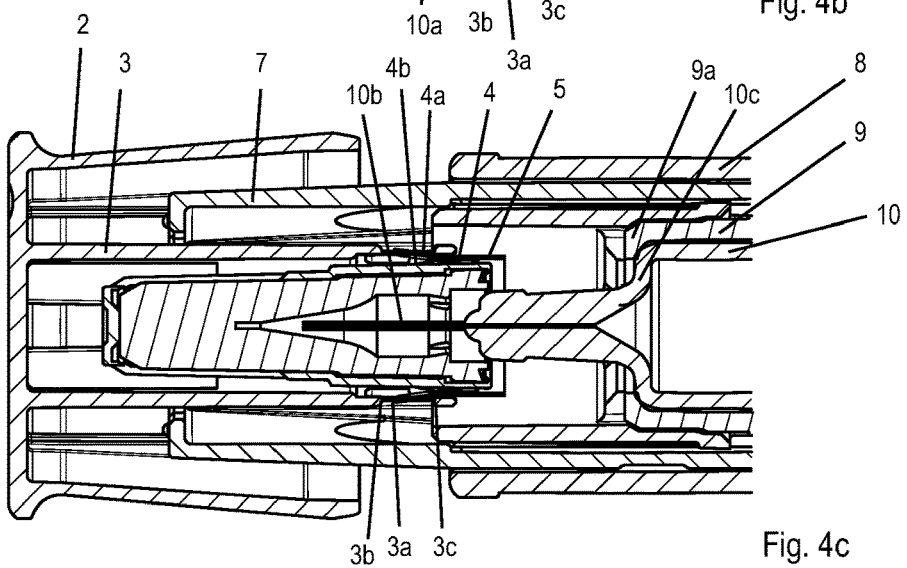

FIGS. 4a to 4c provide longitudinal cross-sectional views of the distal part of the injection device of FIG. 1, showing the removal of the cap (FIG. 1; 1) from the injection device.

When removing the cap (1) from the housing (8) and/or the needle protection sleeve (7), the user may grip either the grip element (2) or the sleeve element (3). The cap (1) may be removed from the housing (8) or the needle protection sleeve (7) by means of an axial movement in the distal direction, or by means of a combined axial and rotary movement in the distal direction. The sleeve element (3) and the engagement element (4) may be axially movable relative to one another until the engagement element (4), or at least the long leg (4a) of the engagement element (4), comes into a non-positive and/or positive connection and/or engagement, such as a driving engagement, with the proximal edge (3c) of the recess (3a) of the sleeve element (3), for instance as shown by a comparison of FIGS. 4a and 4b. The proximal edge (3c) of the recess (3a) of the sleeve element (3) and the engagement element (4), or at least the long leg (4a) of the engagement element (4), may form the non-positive and/or the positive connection and/or the engagement, such as a driving engagement. The engagement element (4), or at least the long leg (4a) of the engagement element (4), may be moved, such as undeformed, deformed or radially inwardly deformed, by the proximal edge (3c) of the sleeve element (3). The engagement element (4), or at least the long leg (4a) of the engagement element (4), may be moved, such as pressed, pretensioned or deformed, against the needle shield cap (10a) of the product container (10) by the proximal edge (3c) of the sleeve element (3). The engagement element (4), or at least the short leg (4b) of the engagement element (4), may engage or bite on or in the needle shield cap (10a), such as engage or bite on or in a lateral surface, an edge, a distal end face, or a proximal face end of the needle shield cap (10a) via a tip of the short leg (4b). The cap (1) may thus be axially fixedly connected to the needle shield cap (10a) at least in the distal direction, such as axially fixedly connected in a driving engagement, for instance as shown in FIG. 4b. In the engagement position of the engagement element (4), the engagement element (4) may be axially fixedly connected to the needle shield cap (10a), with the needle shield cap (10a) being carried along by the engagement element (4) of the cap (1) during continued axial movement of the cap (1), for instance as shown in FIG. 4c. The needle shield cap (10a) may remain in the sleeve element (3) due to the engagement element (4), or at least due to the engagement with the short leg (4b) of the engagement element (4) and/or the holding element (6), and can be disposed of. The injection device is now prepared for an injection.

REFERENCE SIGNS

1 Cap
2 Grip element
3 Sleeve element
3a Recess of the sleeve element
3b Distal edge of the recess of the sleeve element
3c Proximal edge of the recess of the sleeve element
4 Engagement element
4a Long legs of the engagement element
4b Short legs of the engagement element
5 Remover element
6 Holding element
7 Needle protection sleeve
8 Housing
9 Product container holder
9a Shoulder of the product container holder
10 Product container
10a Needle shield cap
10b Injection needle
10c Product container portion
10d Flange of product container
L Longitudinal axis

What is claimed is:

1. An injection device with a longitudinal axis, comprising:
   a housing for receiving a product container, wherein the product container includes an injection needle fixedly connected thereto and a needle shield cap detachably arranged on the product container, the needle shield cap enclosing the injection needle and sealing the injection needle from the environment in a sterile manner; and
   a cap detachably connected to a distal end of the housing, wherein the cap comprises an engagement element for removing the needle shield cap from the product container when the cap is removed from the injection device, wherein the engagement element is deformable such that the engagement element is movable from a spaced-apart position in which the engagement element is radially spaced from the needle shield cap to an engagement position in which the engagement element is in an engagement with the needle shield cap, wherein the engagement element is deformed during cap removal,
   wherein the cap comprises a sleeve element, the sleeve element comprising a recess having a distal edge and a proximal edge, wherein in the spaced-apart position, the engagement element extends from an interior of the sleeve element through the recess and rests on the distal edge of the recess at an exterior of the sleeve element, and wherein the engagement element is moved to the engagement position by the proximal edge of the recess.

2. The injection device according to claim 1, wherein the sleeve element comprises a grip element to be gripped by a user.

3. The injection device according to claim 1, wherein the sleeve element and the engagement element are axially movable relative to one another when the engagement element is in the spaced-apart position.

4. The injection device according to claim 3, wherein the sleeve element and the engagement element are axially fixed relative to one another at least in a distal direction when the engagement element is in the engagement position.

5. The injection device according to claim 4, wherein the sleeve element and the engagement element are axially movable relative to one another when the engagement element moves from the spaced-apart position into the engagement position.

6. The injection device according to claim 5, wherein the engagement element is plastically and/or elastically deformable.

7. The injection device according to claim 1, wherein the sleeve element and the engagement element are axially fixed relative to one another at least in a distal direction when the engagement element is in the engagement position.

8. The injection device according to claim 1, wherein the engagement element is plastically and/or elastically deformable.

9. The injection device according to claim 1, wherein the engagement element comprises a hook-shape.

10. The injection device according to claim 9, wherein the engagement element comprising the hook-shape further comprises a long leg and a short leg, and wherein, in the spaced-apart position, the long leg of the engagement element is undeformed, deformed or radially outwardly deformed.

11. The injection device according to claim 10, wherein in the engagement position, the long leg of the engagement element is undeformed, deformed or radially inwardly deformed.

12. The injection device according to claim 11, wherein the sleeve element and the engagement element are axially movable relative to one another when the engagement element is in the spaced-apart position, and are axially fixed relative to one another at least in a distal direction when the engagement element is in the engagement position.

13. A method for assembling an injection device and/or preparing an injection device for the administration of a product, comprising the steps of:
   providing a housing for receiving a product container;
   providing a cap releasably attached to a distal end of the housing, wherein the cap comprises an engagement element for removing a needle shield cap from the product container when the cap is removed from the injection device, wherein the cap comprises a sleeve element with a recess having a distal edge and a proximal edge, and the engagement element extends from an interior of the sleeve element through the recess and rests on the distal edge of the recess at an exterior of the sleeve element, wherein the engagement element is at least partially undeformed, deformed or radially outwardly deformed by the distal edge of the recess;
   attaching the cap to the distal end of the housing such that the sleeve element and the engagement element are axially movable relative to one another;
   providing a product container comprising an injection needle fixedly connected thereto, wherein a needle shield cap is detachably arranged on the product container, the needle shield cap surrounding the injection needle and sealing the injection needle from the environment in a sterile manner; and
   shifting or inserting the product container with the detachably connected needle shield cap into the housing in a distal direction along a longitudinal axis of the housing, wherein the engagement element is undeformed, deformed or radially outwardly deformed in such a way that during displacement of the product container relative to the housing in the distal direction, the needle shield cap is radially spaced apart from the engagement element or becomes further radially spaced apart from the engagement element.

14. The method of claim 13, wherein the engagement element is deformable such that during removal of the cap from the injection device, the engagement element is brought into an engagement with the needle shield cap, and wherein the engagement element is, at least partially undeformed, deformed or radially inwardly deformed by the proximal edge of the recess.

15. The method of claim 14, wherein the engagement element is plastically and/or elastically deformed.

16. A method for assembling an injection device and/or preparing an injection device for the administration of a product, comprising the steps of:
  providing a housing for receiving a product container with an injection needle;
  providing an engagement element, wherein the engagement element is deformable for removing a needle shield cap detachably attached to the product container;
  holding the housing and the engagement element on a first assembly tool;
  connecting in a frictional and/or positive connection, a sleeve element comprising a recess having a distal and a proximal edge with a needle protection sleeve, wherein the needle protection sleeve protrudes over a distal end of the injection needle; and
  assembling the sleeve element and the engagement element such that the engagement element extends from an interior of the sleeve element through the recess and rests on the distal edge of the recess at an exterior of the sleeve element.

17. The method of claim 16, wherein during the assembling step, a portion of a second assembly tool deforms the engagement element such that the engagement element rests on the distal edge of the recess of the sleeve element.

18. The method of claim 17, wherein the first assembly tool comprises a mandrel and wherein the second assembly tool comprises a spreader tool.

19. The method of claim 16, wherein the engagement element is deformable such that during removal of the cap from the injection device, the engagement element is brought into an engagement with the needle shield cap, and wherein the engagement element is, at least partially, undeformed, deformed or radially inwardly deformed by the proximal edge of the recess.

20. The method of claim 19, wherein the engagement element is plastically and/or elastically deformed.

* * * * *